United States Patent [19]

Hulek et al.

[11] Patent Number: 4,534,405
[45] Date of Patent: Aug. 13, 1985

[54] METHOD AND AN ARRANGEMENT FOR INSPECTING THE SURFACE OF STEEL STOCK HAVING A TEMPERATURE ABOVE THE CURIE POINT

[75] Inventors: Anton Hulek, Linz; Wolfgang Polanschütz, Leoben, both of Austria

[73] Assignee: Voest-Alpine Aktiengesellschaft, Linz, Austria

[21] Appl. No.: 461,268

[22] Filed: Jan. 26, 1983

[30] Foreign Application Priority Data

Feb. 11, 1982 [AT] Austria ............................ 515/82

[51] Int. Cl.³ .............................................. B22D 2/00
[52] U.S. Cl. ...................................... 164/451; 164/150; 324/203; 324/228
[58] Field of Search ............... 164/451, 452, 150, 154, 164/4.1; 324/224, 228, 203

[56] References Cited

U.S. PATENT DOCUMENTS

| 2,970,256 | 1/1961 | Sazynski .................... 324/34 |
| 3,512,401 | 5/1970 | Thalmann ................ 164/451 X |
| 4,408,160 | 10/1983 | King et al. ................... 324/228 |

FOREIGN PATENT DOCUMENTS

| 2457670 | 6/1976 | Fed. Rep. of Germany . |
| 2600453 | 7/1976 | Fed. Rep. of Germany . |
| 421393 | 3/1967 | Switzerland . |
| 443576 | 2/1968 | Switzerland . |
| 2008259 | 5/1979 | United Kingdom . |

OTHER PUBLICATIONS

Godshall et al., Eddy Current Inspection of Pipe At 2150 Deg. F., American Society of Mechanical Engineers (Exrs. search room 324-224).

Primary Examiner—Nicholas P. Godici
Assistant Examiner—C. McKee
Attorney, Agent, or Firm—Horst M. Kasper

[57] ABSTRACT

There is disclosed a method and arrangement for inspecting the surface of steel stock having a temperature above the Curie point. In order to detect, with a great certainty and accuracy, defects in the hot steel stock, with a loss of energy for cooling the steel stock for inspection and subsequently reheating it for further processing being avoided, only a thin surface layer of the steel stock is intensively cooled on the surface to be inspected, to a temperature below the Curie point. The core of the steel remains hot. Immediately thereafter, a magnetic or electromagnetic field is induced in the cooled surface layer and disturbances in the induced field caused by defects in the steel stock are detected and recorded by pick-ups.

13 Claims, 6 Drawing Figures

METHOD AND AN ARRANGEMENT FOR INSPECTING THE SURFACE OF STEEL STOCK HAVING A TEMPERATURE ABOVE THE CURIE POINT

The invention relates to a method for inspecting the surface of steel stock having a temperature above the Curie point, in particular for continuously inspecting the surface of continuously cast steel strands, as well as to an arrangement for carrying out the method.

For inspecting the surfaces of hot slabs, various methods are known (Stahl und Eisen, 101, 1981, pp. 1135 to 1137 and 1183 to 1188), yet none of these methods has succeeded in operation.

The optical method, which may be considered the most suited one for hot slabs, makes no difference between harmless irregularities of the slab surface and actual defects, which can be detected as such only from a certain size (length and width). Furthermore, it is impossible to recognize defect depths and to detect defects that are covered by the surface.

Furthermore, the eddy-current method has been applied to hot slabs, yet considerable disadvantages have come up in the practical application of this method, which are due to the deterioration of the signal-to-noise ratio on account of the coarseness of the inspected surface as well as to magnetic inhomogeneities, which, however, may also be due to cooling problems of the testing probes provided in the immediate vicinity of the hot surfaces.

Magnetic stray-flux techniques are not suitable for steel stock hotter than the Curie point, since they require ferromagnetic material.

The invention aims at avoiding the disadvantages of the known methods and has as its object to provide a method, as well as an arrangement for carrying out the method, which make it possible to detect with a great certainty and accuracy defects in the hot steel stock, i.e. with the same certainty as with cold steel stock, wherein, however, a loss of energy as occurs when cooling the steel stock for inspection and subsequently reheating it for further processing (e.g. hot rolling) is avoided.

This object is achieved according to the invention in that only a thin surface layer of the steel stock is intensively cooled on the surface to be inspected, to a temperature below the Curie point, while the core of the steel stock remains hot, whereupon, immediately thereafter, a magnetic or electromagnetic field is induced in the cooled surface layer and disturbances in the induced field caused by defects, in particular cracks, in the steel stock are detected and recorded by means of pick-ups.

The intensive cooling of a surface layer to a temperature below the Curie point, for one part, results in a magnetically homogenous surface layer to be inspected (it cannot happen that regions on the edges have been cooled down to a temperature below the Curie point, while other regions in the side faces of the steel stock have temperatures above the Curie point), and, for the other part, cause the means inducing a field as well as the probes and coils for influencing this field to be subjected to substantially lower temperatures than so far, so that disturbances caused by too strong a thermal load on these means will be prevented. By the intensive cooling of only a thin surface layer, only very little energy of the steel stock gets lost. Apart from very few high-alloyed steel types, an influence on the material properties is not recognizable, since the intensively cooled surface layer still is within a temperature region for soft-annealing or stress-free annealing and is reheated to approximately the temperature prior to cooling, immediately after the surface inspection from the core of the steel stock.

There are various methods for inducing a field and determining its disturbances, for instance the stray-flux method, in particular the high-energy stray-flux method, which have not been considered so far for a surface inspection of steel stock hotter than the Curie point, since these methods necessitate ferromagnetic material. Furthermore, the eddy-current method, in particular the eddy-current rotating-probe method, is suited for this purpose. Preferably, the induction of a field and the determination of its disturbances can be carried out by means of a magnetically inductive method.

According to a preferred embodiment, an electromagnetically excited ultrasonics is used.

Advantageously, the surface of the hot steel stock is cooled to about 500° to 700° C., the depth of the surface layer of the steel stock cooled to below the Curie point extending as far as to at least 1 mm and at most 5 mm below the surface of the steel stock.

For continuously cast steel strands, the intensive cooling suitably is carried out immediately after the complete solidification of the strand having a surface temperature of between 800° and 1,000° C.

An arrangement for carrying out the method according to the invention is characterized in that a means for spraying coolant onto the surface to be inspected is arranged at a distance from the surface and a means for inducing the field and pick-ups detecting its disturbances are provided at a slight distance therefrom, in the strand extraction direction.

An arrangement for continuously cast steel strands, in particular for steel slabs, is characterized in that, between the driving rolls and the strand separating means, which are provided on the end side of the continuous casting plant, jet beams extending transversely over the strand and including jets directed towards the surface of the strand are provided, and that the means inducing the field is provided at a slight distance from the jet beams, in the strand extraction direction. An inspection of the continuously cast steel strands may be necessary for the purpose of higher casting speeds, even after the division of the strand into sections of predetermined lengths, wherein in this case the arrangement of the invention is arranged behind the strand separating means.

The invention will now be explained in more detail by way of several exemplary embodiments and with reference to the accompanying drawings, wherein.

Figure 1:
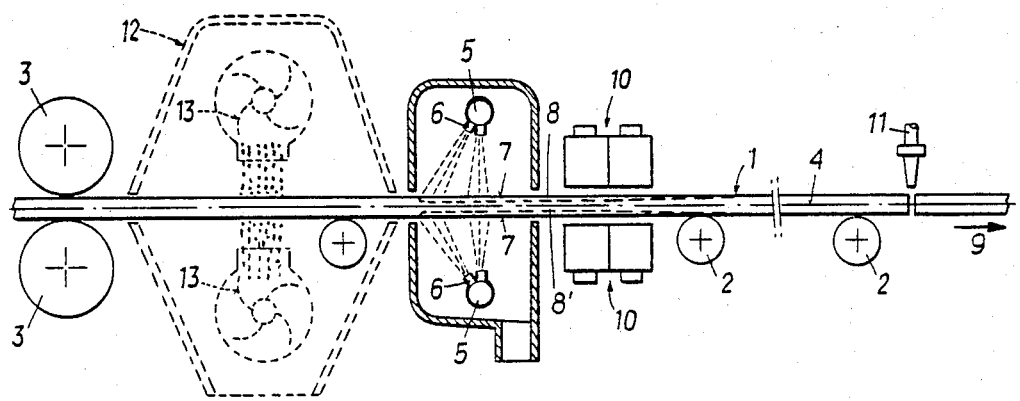
FIG. 1 is a side view in a schematic illustration.
Figure 2:
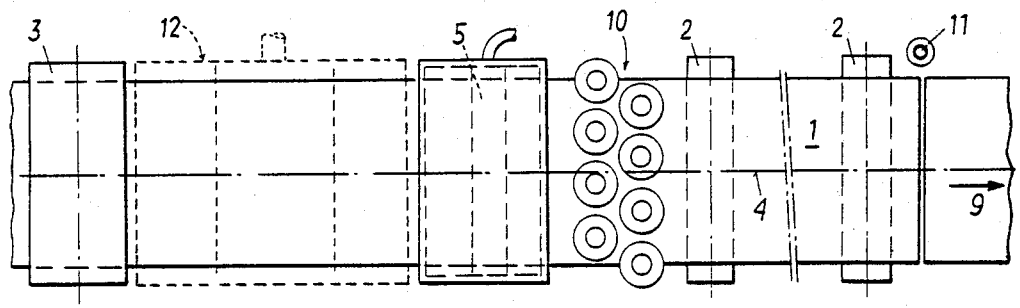
FIG. 2 is a ground plan in a schematic illustration, of an arrangement for carrying out the method according to the invention for continuously cast steel strands.
Figure 3:
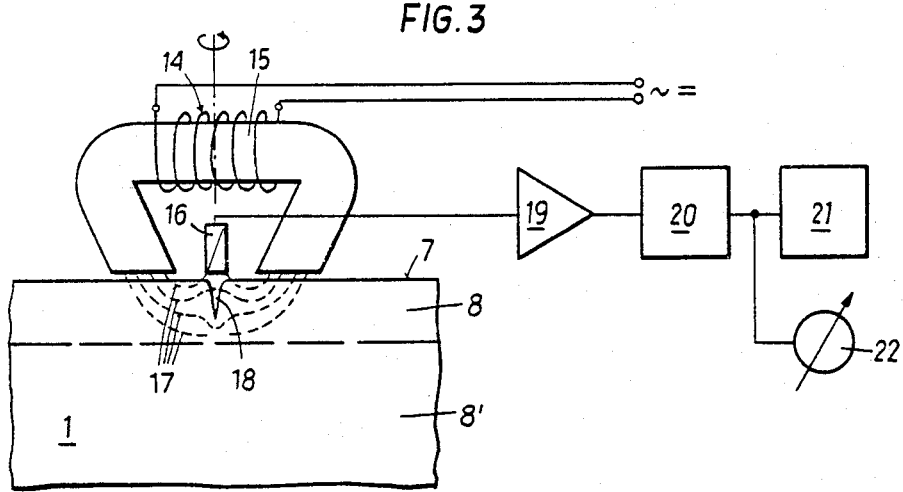
FIGS. 3, 4, 5 and 6 illustrate in detail different methods for inducing a field and determining its disturbances by defects.

By 1 a strand having a slab cross section is denoted, which emerges from a continuous casting plant, from which merely the driving rolls 3 arranged end-sidely before the run-out rollerway 2 are illustrated. After the strand has passed the gap formed by the driving rolls 3, the strand 1 already is completely solidified and, as a rule, has a surface temperature of more than 800° C. Closely behind the driving rolls 3, two jet beams 5 extending transversely to the strand longitudinal axis 4 for a coolant, such as water, are arranged in a casing, i.e. one above and one below the strand 1. The coolant leaving the jets 6 of the jet beams 5 impinges on the strand surfaces that constitute the broad sides 7 of the strand 1, cooling the same to a temperature below the Curie point. The amount of coolant is controlled in dependence on the strand casting speed in a manner that a surface layer 8, whose thickness is between 1 and 5 mm, is cooled to a temperature below the Curie point, the temperature of the broad side surfaces 7 of the strand 1 being cooled to between 500° and 700° C. During this intensive cooling, the temperature of the core 8' of the steel stock 7 changes only negligibly; it remains approximately equally hot.

In the extraction direction 9 a means for inducing a field and determining its disturbances by defects of the strand surface is arranged immediately behind the jet beams 5, which means is generally denoted by 10 and is going to be explained in more detail in the following by way of FIGS. 3 to 6. Following upon this means 10, the strand separating means 11 for shearing the strand 1 to length is provided. Between the run-out side driving rolls 3 and the jet beams 5, a descaling means 12 may be provided, which descaling means, as illustrated in FIG. 1 by dash lines, comprises flinger wheels 13 flinging steel scrap or the like against the broad sides 7 of the strand 1. Descaling and intensive cooling may be effected also simultaneously by a wet-blasting method comprising the components blasting agent, water and compressed air.

The means 10 for the detection of defects proper will be explained in more detail in FIGS. 3 to 6, FIG. 3 schematically illustrating the high-energy stray-flux method. A field coil 14 of a rotating yoke 15 is supplied with direct or alternating current. A magnetic-field-intensive probe is denoted by 16. The field lines induced by the yoke 15 in the surface layer 8, which has been cooled to a temperature below the Curie point thus having a permeability of more than "1", are denoted by the reference numerals 17. The field line course disturbed by a crack 18 in the stand surface 7 also has been entered. The disturbance of the magnetic field by the crack 18 is picked up by the magnetic-field-intensive probe 16 and transmitted to signal-processing and monitoring devices 21 or 22 via an amplifier 19 and a filter 20.

Figure 4:
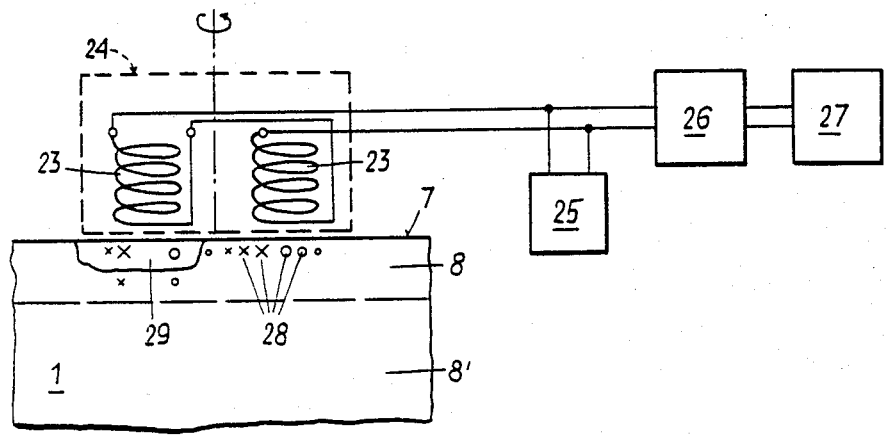

The eddy-current method is going to be explained in more detail by way of FIG. 4. Coils 23 are provided in rotating and cooled probes 24, the coils 23 being connected to an oscillator 25 as well as to a phase measuring bridge 26 or an amplifier. The means that process further and monitor a signal from the coils 23 are schematically illustrated and denoted by 27. The eddy current 28 induced also is schematically entered in FIG. 4. Its disturbance by a defect 29 in the surface layer 8, which has been cooled to a temperature below the Curie point, is shown in the left-hand part of FIG. 4.

Figure 5:
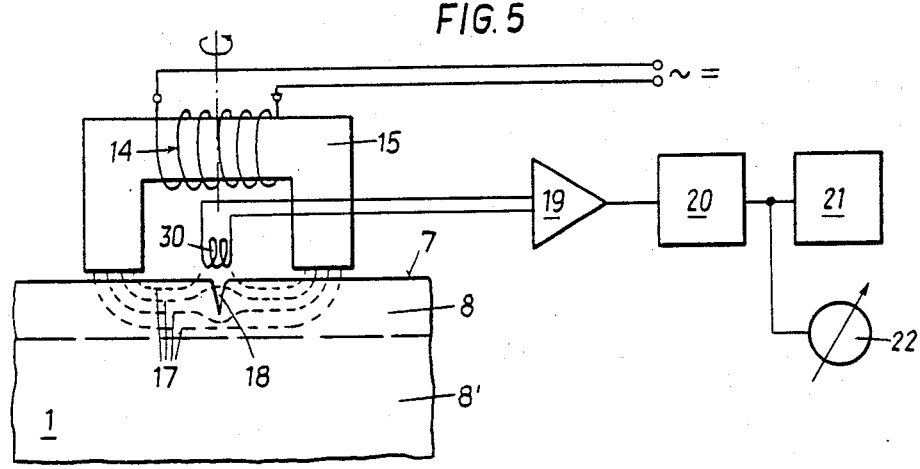

The magnetically inductive technique is illustrated in FIG. 5. Basically, it corresponds to the stray-flux method illustrated in FIG. 3, yet a pick-up coil 30 is provided instead of a magnetic-field-intensive probe.

Figure 6:
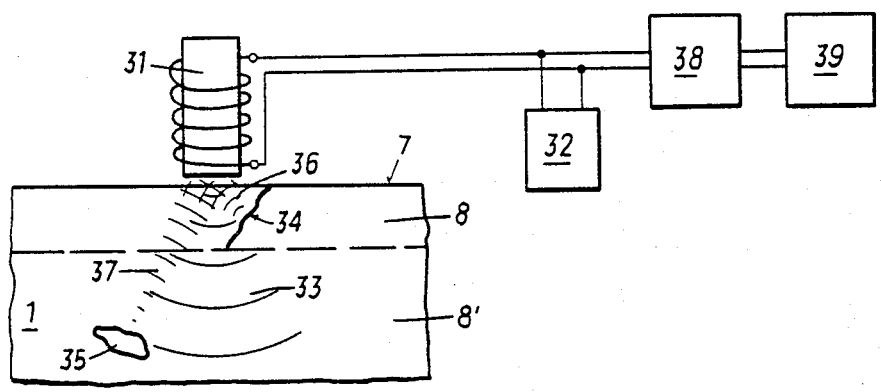

According to the method illustrated in FIG. 6, electromagnetically excited ultrasonics may be used.

In principle, an ultrasonic converter is comprised of a coil or antenna. A coil as illustrated for example in FIG. 6 when passed by a current acts like any electrical conductor and generates a magnetic field. If the current is an alternating current, then an alternating electromagnetic field is generated in the surrounding area in accordance with Maxwell's equations. The geometrical construction of a coil with a number of parallel windings has the effect of coherently superposing the fields of the individual windings and thus to increase the field strength achievable in the surrounding area based on a certain size of electrical current passing through a conductor.

An alternating electromagnetic field propagates and can penetrate into solid into said materials such as for example steel. The electromagnetic field generated by the alternating current passing through the coil penetrates into the surface layer of the hot metal cooled to a temperature below the Curie point, again following the equations set forth by Maxwell.

This surface layer of the metal comprises free eletrons. The alternating electromagnetic field penetrating into the surface layer exerts a force onto these free electrons and accelerates them. This Lorentzian force is particularly large in case of materials with a high permeability and depends on the size of the permeability. Steel is a material with a permeability which is a multiple of that of a gas filled space and which depends strongly on the electromagnetic field strength. A correspondingly high Lorentzian force causes accelerated electrons to transfer part of their kinetic energy to the atoms of the crystal lattice and if this occurs in a coherent fashion, then mechanical vibrations and waves are generated in the material. If the frequency of the exciting field is sufficiently high, then the mechanical vibrations represent ultrasonic waves.

A general theory of such phenomina is known to some extent. For example, the textbook J. M. Ziman: "Principles of the Theory of Solids", Cambridge University Press, London, England, 1965 in the chapter entitled "The Fermi Surface" includes a subchapter 9.5 on page 267 "Magneto-acoustical oscillations". Remarkably, the second paragraph of this chapter starts as follows: "These phenomina are exceedingly complex, in theory and in practice; . . . ".

In case cracks occur in steel material, then the Fermi surface becomes disturbed as fas as it is still possible to employ such concept and a change is caused in the ultrasonic vibration pattern.

These changes are then recorded in an electromechanical converter.

With reference to FIG. 6, an electromagnetic ultrasonics head 31, which is connected to an oscillator 32, is positioned closely above the strand surface 7. By this testing head not only external defects, i.e. defects that reach as far as to the strand surface, but also defects that are located in the layer 8' that has not been cooled to a temperature below the Curie point, i.e. has a permeability of about 1, are detected. The sound field 33 and the sound fields reflected by the defects 34, 35 are schematically entered and denoted by 36 and 37. The evaluation circuit is denoted by 38 and a means for processing further and monitoring signals is denoted by 39.

What we claim is:

1. A method for inspecting the surface of continuously cast steel stock having a temperature above the Curie point and including a hot core and a surface layer which method comprises the steps of intensively cooling only a slight depth of said surface layer at said surface to be inspected to a temperaure below the Curie point and above 500° C. with a substantial portion of the core remaining at a temperature above the Curie point, inducing a magnetic field in the cooled surface layer immediately afterwards, and detecting and recording, by means of pick-ups, disturbances of said magnetic field caused by defects in said steel stock.

2. A method as set forth in claim 1, wherein said field is an electromagnetic field.

3. A method as set forth in claim 1, wherein said defects in said steel stock are cracks.

4. A method as set forth in claim 1 or 2, wherein inducing said field and detecting its disturbances is effected by a stray-flux method.

5. A method as set forth in claim 1 or 2, wherein inducing said field and detecting its disturbances is effected by a high energy stray-flux method.

6. A method as set forth in claim 2, wherein inducing said field and detecting its disturbances is effected by an eddy-current method.

7. A method as set forth in claim 2, wherein inducing said field and detecting its disturbances is effected by an eddy-current rotating-probe method.

8. A method as set forth in claim 2, wherein inducing said field and detecting its disturbances is effected by a magnetically inductive method.

9. The method for inspecting the surface of continuously cast steel stock having a temperature above the Curie point and including a core and a surface layer according to claim 1 wherein the induced magnetic field is an electromagnetically excited field and wherein disturbances of said induced magnetic field caused by defects in said steel stock are detected and recorded electromagnetically via an ultrasonic vibration field generated in the steel stock by the electromagnetic field.

10. A method as set forth in claim 1 or 9, wherein said surface layer of said hot steel stock is cooled to about 500° to 700° C., the depth of said surface layer of said steel stock, that has been cooled to below the Curie point extending as far as to at least 1 mm and at most 5 mm below the surface.

11. A method as set forth in claim 1 or 9 to be applied for continuously cast steel strands, wherein said intensive cooling of said surface layer is carried out immediately after solidification of said steel strands having a surface temperature of between 800° and 1,000° C.

12. An arrangement for inspecting the surface of steel stock, including steel strands, having a temperature above the Curie point, which arrangement comprises spraying means arranged at a distance from the surface to be inspected and adapted for spraying coolant thereon so as to obtain a thin surface layer cooled to below the Curie point and above 500° C. while a core remains hot, electromagnetic field inducing means arranged at a slight distance from the said spraying means in the strand extraction direction and adapted for inducing an electromagnetic field in said cooled thin surface layer, and pickups provided for detecting disturbances caused in resulting wave fields by defects in said steel stock.

13. An arrangement provided in a continuous casting plant for inspecting the surface of a continuously cast steel strand having a temperature above the Curie point, in particular a steel slab, which arrangement comprises driving rolls arranged on the end side of the continuous casting plant, a strand separation means arranged at a distance therefrom, jet beams provided between said driving rolls and said strand separation means and extending transversely over the strand, said jet beams including jets directed towards said surface of said steel strand and spraying coolant onto said surface so as to obtain a thin surface layer cooled to below the Curie point and above 500° C., and field inducing means arranged at a slight distance from said jet beams in the strand extraction direction and adapted for inducing a field in said cooled surface layer, and pick-ups provided for detecting disturbances caused in said field by defects in said steel stock.

* * * * *